United States Patent
Li et al.

(10) Patent No.: US 11,847,766 B2
(45) Date of Patent: Dec. 19, 2023

(54) METHOD AND DEVICE FOR DETECTING BRIGHT SPOTS ON IMAGE, AND COMPUTER PROGRAM PRODUCT

(71) Applicant: GENEMIND BIOSCIENCES COMPANY LIMITED, Shenzhen (CN)

(72) Inventors: Linsen Li, Shenzhen (CN); Weibin Xu, Shenzhen (CN); Huan Jin, Shenzhen (CN); Zefei Jiang, Shenzhen (CN); Zhiliang Zhou, Shenzhen (CN); Qin Yan, Shenzhen (CN)

(73) Assignee: GENEMIND BIOSCIENCES COMPANY LIMITED, Shenzhen (CN)

( * ) Notice: Subject to any disclaimer, the term of this patent is extended or adjusted under 35 U.S.C. 154(b) by 497 days.

(21) Appl. No.: 17/270,413

(22) PCT Filed: Aug. 22, 2018

(86) PCT No.: PCT/CN2018/101818
§ 371 (c)(1),
(2) Date: Feb. 22, 2021

(87) PCT Pub. No.: WO2020/037573
PCT Pub. Date: Feb. 27, 2020

(65) Prior Publication Data
US 2021/0217177 A1    Jul. 15, 2021

(51) Int. Cl.
*G06T 7/62* (2017.01)
*G06T 5/00* (2006.01)
(Continued)

(52) U.S. Cl.
CPC .............. *G06T 5/002* (2013.01); *G06T 5/003* (2013.01); *G06T 7/0012* (2013.01); *G06T 7/136* (2017.01); *G06T 7/194* (2017.01); *G16B 35/00* (2019.02)

(58) Field of Classification Search
CPC .......... G06N 3/084; G06N 3/08; G06N 3/082; G06N 3/04; G06N 3/044; G06N 3/045;
(Continued)

(56) References Cited

U.S. PATENT DOCUMENTS

| | | |
|---|---|---|
| 2013/0165328 A1 | 6/2013 | Previte |
| 2014/0270459 A1* | 9/2014 | Moll ................ G01N 21/6428 427/256 |

(Continued)

FOREIGN PATENT DOCUMENTS

| | | |
|---|---|---|
| CN | 101206116 A | 6/2008 |
| CN | 101930116 A | 12/2010 |

(Continued)

OTHER PUBLICATIONS

Ye Binggang, High-throughput Genome Sequencing Image Processing and Data Analysis, China doctoral dissertation full text database, vol. 11, p. 34-35, 46-49, Nov. 15, 2010.
(Continued)

*Primary Examiner* — Quan M Hua
(74) *Attorney, Agent, or Firm* — Dilworth IP, LLC

(57) ABSTRACT

A method and device for detecting bright spots on an image. The image is acquired from a field of view where a base extension reaction occurs, multiple nucleic acid molecules with optically detectable labels exist in the field of view where the base extension reaction occurs, and at least some of the nucleic acid molecules appear as bright spots on the image. The method includes preprocessing the image to obtain a preprocessed image; determining a critical value to
(Continued)

simplify the preprocessed image to obtain a simplified image, determining a first bright spot detection threshold on the basis of the preprocessed image, and identifying candidate bright spots on the image on the basis of the preprocessed image and the simplified image, including determining a pixel matrix that satisfies at least two of conditions as a candidate bright spot.

17 Claims, 3 Drawing Sheets

(51) Int. Cl.
  *G06T 7/136* (2017.01)
  *G06T 7/194* (2017.01)
  *G16B 35/00* (2019.01)
  *G06T 7/00* (2017.01)

(58) Field of Classification Search
  CPC ........ G06N 3/048; G06N 3/063; G06N 3/088; G06N 5/022; G06N 5/04; G06N 5/046; G06N 5/048; G01N 21/6454; G01N 27/27; G01N 27/3275; G01N 21/6428; G01N 2333/55; G01N 2458/10; G01N 2500/00; G01N 33/5306; G01N 33/54366; G01N 33/57419; G01N 33/587; G01N 33/6803; G06V 10/82; G06V 10/454; G06V 20/698; G06V 2201/03; G06V 10/267; G06V 10/28; G06V 10/30; G06V 10/42; G06V 10/44; G06V 10/751; G06V 10/762; G06V 10/809; G06V 10/993; G06V 20/47; G06V 20/69; G06V 2201/04; G06V 30/19107; G06T 2207/30072; G06T 5/002
  See application file for complete search history.

(56) References Cited

U.S. PATENT DOCUMENTS

| | | | |
|---|---|---|---|
| 2014/0349281 | A1 | 11/2014 | Jennings |
| 2015/0317433 | A1 | 11/2015 | Kermani et al. |

FOREIGN PATENT DOCUMENTS

| | | | |
|---|---|---|---|
| CN | 101950419 | A | 1/2011 |
| CN | 102174384 | A | 9/2011 |
| CN | 102354398 | A | 2/2012 |
| CN | 102663720 | A | 9/2012 |
| CN | 103582697 | A | 2/2014 |
| CN | 104297249 | A | 1/2015 |
| CN | 104318568 | A | 1/2015 |
| CN | 104376537 | A | 2/2015 |
| CN | 105039147 | A | 11/2015 |
| CN | 105205788 | A | 12/2015 |
| CN | 105303533 | A | 2/2016 |
| CN | 105389581 | A | 3/2016 |
| CN | 105524827 | A | 4/2016 |
| CN | 105551034 | A | 5/2016 |
| CN | 105741266 | A | 7/2016 |
| CN | 106295124 | A | 1/2017 |
| CN | 107918931 | A | 4/2018 |
| CN | 107945150 | A | 4/2018 |
| CN | 108192953 | A | 6/2018 |
| CN | 108229098 | A | 6/2018 |
| EP | 3306566 | A1 | 4/2018 |
| JP | 2007315772 | A | 12/2007 |
| KR | 101348680 | B1 | 1/2014 |
| WO | 2016107896 | A1 | 7/2016 |
| WO | WO-2016120440 | A1 * | 8/2016 ......... G06K 9/00127 |

OTHER PUBLICATIONS

Julien Ghaye et al., Image Thresholding Techniques for Localization of Sub-Resolution Fluorescent Biomarkers, International Society for Advancement of Cytometry (ISAC), Cytometry Part A, 83A, p. 1001-1016, 2013.

Feng He et al., A Laplacian of Gaussian-Based Approach for Spot Detection in Two-Dimensional Gel Electrophoresis Images, 4th Conference on Computer and Computing Technologies in Agriculture (CCTA), Nanchang, China, 10.1007/978-3-642-18369-0_2. hal-01564853, 9 pages, Oct. 2010.

Ihor Smal, Quantitative Comparison of Spot Detection Methods in Fluorescence Microscopy, IEEE Transactions on Medical Imaging, vol. 29, No. 2, p. 282-301, Feb. 2010.

Kenji Takita et al., High-Accuracy Subpixel Image Registration Based on Phase-Only Correlation, IEICE Trans. Fundamentals, vol. E86-A, No. 8, Aug. 2003.

International Search Report for PCT/CN2019/101818; dated May 20, 2019, 2 pages.

Extended European Search Report for App. No. EP18931064.2, dated Jul. 2, 2021, 12 pages.

Julien Ghaye et al: "Image Thresholding Techniques for Localization of Fluorescent Biomarkers", NIH Public Access Author Manuscript, vol. 83, No. 11, Sep. 16, 2013 (Sep. 16, 2013), pp. 1001-1016.

* cited by examiner

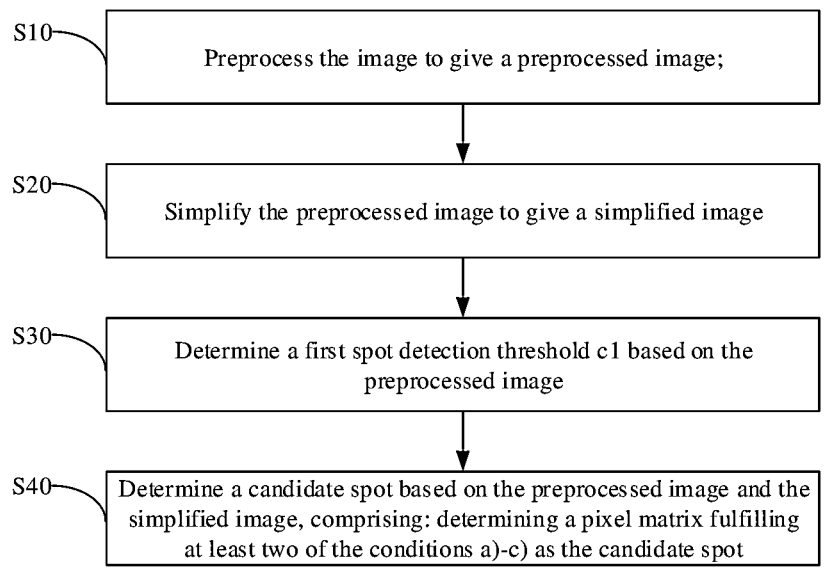

METHOD AND DEVICE FOR DETECTING BRIGHT SPOTS ON IMAGE, AND COMPUTER PROGRAM PRODUCT

TECHNICAL FIELD

The present disclosure relates to the field of image processing, and in particular, to a method for detecting a spot on an image, a device for detecting a spot on an image, and a computer program product.

BACKGROUND

In related technologies, spot location on an image has important applications in both gene sequencer and LED array.

Image analysis is a very important part in a sequencing system based on optical imaging, for example, nucleic acid sequencing. The nucleic acid sequencing is implemented based on detection and identification of spots on an image and converting the detected and identified spots into a base/nucleotide sequence. The accuracy of spot detection and location on the image directly determines accuracy of gene sequencing.

In the nucleic acid sequencing application, methods for easily, quickly and/or effectively detecting the spots on the image, and using the spot information or accurately interpreting the spot information still need development and improvement.

SUMMARY

The embodiments of the present disclosure are intended to solve at least one of the technical problems existing in the prior art or at least provide an alternative practical solution.

According to one embodiment of the present disclosure, a method for detecting a spot on an image is provided. The image is acquired from a field of view having a plurality of nucleic acid molecules with optically detectable label in which a base extension reaction occurs, and at least a part of the nucleic acid molecules are presented as spots on the image. The method comprises: preprocessing the image to give a preprocessed image; determining a critical value to simplify the preprocessed image, so as to give a simplified image, comprising: assigning a first preset value to a pixel value of a pixel on the preprocessed image less than the critical value, and a second preset value to a pixel value of a pixel on the preprocessed image not less than the critical value; determining a first spot detection threshold c1 based on the preprocessed image; and identifying a candidate spot on the image based on the preprocessed image and the simplified image, comprising: determining a pixel matrix fulfilling the following conditions as a candidate spot: a) in the preprocessed image, the center pixel of the pixel matrix has the maximum pixel value, the pixel matrix is represented by k1×k2, both k1 and k2 are odd numbers greater than 1, and the pixel matrix k1×k2 comprises k1×k2 pixels; b) in the simplified image, the pixel value of the center pixel of the pixel matrix is the second preset value, and the pixel connectivity in the pixel matrix is greater than ⅔×k1×k2; and c) in the preprocessed image, the pixel value of the center pixel of the pixel matrix is greater than a third preset value, g1*g2 is >c1, g1 is a correlation coefficient of two-dimensional Gaussian distribution in an area of m1×m2 centered on the center pixel of the pixel matrix, g2 is a pixel matrix in the area of m1×m2, both m1 and m2 are odd numbers greater than 1, and the area of m1×m2 comprises m1×m2 pixels.

According to another embodiment of the present disclosure, an device for detecting a spot on an image is provided. The device is configured for implementing the method for detecting a spot on an image in the above embodiment of the present disclosure. The image is acquired from a field of view having a plurality of nucleic acid molecules with optically detectable label in which a base extension reaction occurs, and at least a part of the nucleic acid molecules are presented as spots on the image. The device comprises: a preprocessing unit configured for preprocessing the image to give a preprocessed image; a simplification unit configured for: determining a critical value to simplify the image preprocessed by the preprocessing unit, so as to give a simplified image, comprising: assigning a first preset value to a pixel value of a pixel on the preprocessed image less than the critical value, and a second preset value to a pixel value of a pixel on the preprocessed image not less than the critical value; a first threshold determining unit, configured for determining a first spot detection threshold c1 based on the image preprocessed by the preprocessing unit; and a candidate spot determining unit, configured for identifying a candidate spot on the image based on the image preprocessed by the preprocessing unit and the image simplified by the simplification unit, comprising: determining a pixel matrix fulfilling the following conditions as a candidate spot: a) in the preprocessed image, the center pixel of the pixel matrix has the maximum pixel value, the pixel matrix is represented by k1×k2, both k1 and k2 are odd numbers greater than 1, and the pixel matrix k1×k2 comprises k1×k2 pixels; b) in the simplified image, the pixel value of the center pixel of the pixel matrix is the second preset value, and the pixel connectivity in the pixel matrix is greater than ⅔×k1×k2; and c) in the preprocessed image, the pixel value of the center pixel of the pixel matrix is greater than a third preset value, g1*g2 is >c1, g1 is a correlation coefficient of two-dimensional Gaussian distribution in an area of m1×m2 centered on the center pixel of the pixel matrix, g2 is a pixel matrix in the area of m1×m2, both m1 and m2 are odd numbers greater than 1, and the area of m1×m2 comprises m1×m2 pixels.

According to still another embodiment of the present disclosure, a computer-readable storage medium for storing a program for execution by a computer is provided, wherein the execution of the program comprises implementing the method for detecting a spot on an image in any of the above embodiments. The computer-readable storage medium may include: read-only memory, random access memory, magnetic disk, optical disk, or the like.

According to still another embodiment, a computer program product comprising an instruction for detecting a spot on an image is provided, wherein the instruction causes the computer to execute all or a part of the steps of the spot detection method in any of the above embodiments when the program is executed in the computer.

The "peak" or "spot" is a luminous point on an image, and a luminous point occupies at least one pixel. The "pixel point" is the same as "pixel".

In the embodiments of the present disclosure, the image is from a sequencing platform based on optical imaging including but not limited to the BGI-seq platform (BGI), Illumina/Solexa platform, ABI SOLiD platform (Life Technologies), and Roche 454 platform. The detection of the "spot" is the detection of optical signals of extending bases or base clusters.

According to the method and the device for detecting a spot on an image and the system/computer program product in any of the above embodiments of the present disclosure, spots or peaks on an image can be quickly and effectively detected, especially on an image acquired from a field of view in which a nucleic acid sequencing reaction occurs. There is no special limitation on the to-be-detected image, or original input data. The method is applicable to processing and analysis of any images generated by a nucleic acid sequencing platform based on optical detection, including image quality assessment for focusing and focus tracking, and image processing and analysis for base recognition, and features high accuracy and high efficiency, and more information about the sequence acquired from the image.

It should be noted that currently known spot identification and location method and/or system on a sequencing image is basically developed for images from a second-generation sequencing platform. Most sequencing chips used in the second-generation sequencing are arrays, i.e., probes on the sequencing chip are arranged regularly. Thus, the captured images are pattern images, and signals on the image generally are regular, making accurate identification of effective signals relatively easier. In addition, as the second-generation sequencing generally comprises signal amplification (for example, multiplication) of a nucleic acid template, a nucleic acid template generally exists in a form of a cluster including at least hundreds or thousands of copies. In other words, the signal of the nucleic acid template is a signal set of a large quantity of nucleic acid template molecules. It can be understood that the signal on the image is strong and/or has specific morphological characteristics, or the signal significantly differs from a non-target signal, and is relatively easy for identification and location. Therefore, general spot detection on an image of second-generation sequencing requires no special image processing or comprehensive and high-accurate identification and determination of a spot corresponding to sequence information.

A large quantity of spot signals corresponding to a sequence can be easily acquired, and then identified and converted into the sequence information.

The third-generation sequencing, or single-molecule sequencing, is limited by current development of related technologies of chip surface processing. The sequencing chips used are random chips, i.e., probes on the sequencing chip are randomly arranged. Thus, the captured images are random images, and are not easy for processing and analysis. In addition, as general single molecule sequencing methods do not include a nucleic acid template, the nucleic acid template exists in a form of a single molecule or a few molecules, which are presented in the image as weak and easily interfered/submerged signals. Accurate identification of spots corresponding to nucleic acid molecules and the quantity of identified spots directly determine the off-line throughput and the quantity of effective data. Generally, single molecule sequencing has a high requirement for image processing and spot location that all effective spots on the image are identified and accurately located, so as to provide as much accurate data as possible. The "single molecule" refers to one or a few molecules, for example, no more than 10 molecules. The method and the device for detecting a spot on an image and the corresponding computer product in the embodiments of the present disclosure are applicable to spot detection on a sequencing image, and have specific advantages for random images and signal identification requiring high accuracy.

The additional aspects and advantages of the embodiments of the present disclosure will be partially set forth in the following description, and will partially become apparent from the following description or be appreciated by practice of the embodiments of the present disclosure.

BRIEF DESCRIPTION OF THE DRAWINGS

FIG. 1 is a schematic flowchart of a method for detecting a spot on an image according to a specific embodiment of the present disclosure;

FIG. 2 is a schematic diagram of a pixel matrix and pixel connectivity according to a specific embodiment of the present disclosure;

FIG. 3 is a schematic diagram of corresponding pixel values in an area of m1×m2 centered on the center pixel of a pixel matrix on a simplified image according to a specific embodiment of the present disclosure;

DETAILED DESCRIPTION

Figure 4:
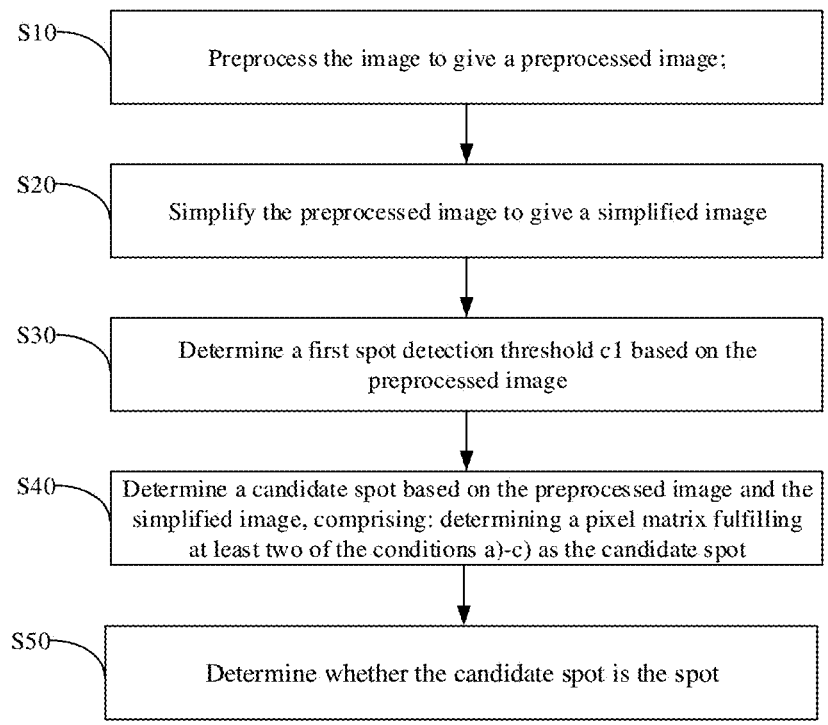
FIG. 4 is a schematic flowchart of a method for detecting a spot on an image according to a specific embodiment of the present disclosure.

The embodiments of the present disclosure are described in detail below, and the examples of the embodiments are shown in the accompanying drawings, throughout which identical or similar reference numerals represent identical or similar elements or elements having identical or similar functions. The embodiments described below by reference to the accompanying drawings are exemplary and are merely intended to explain the present disclosure rather than be construed as limiting the present disclosure.

In the description of the present disclosure, the terms "first", "second", "third" and "fourth" are used for description purpose only rather than construed as indicating or implying relative importance or implicitly indicating the number or sequence of indicated technical features. In the description of the present disclosure, unless otherwise specifically defined, "a plurality of" means two or more than two.

Sequencing (also referred to as sequence determination) in the embodiments of the present disclosure refers to nucleic acid sequencing, including DNA sequencing and/or RNA sequencing, and/or including long fragment sequencing and/or short fragment sequencing.

Sequencing can be performed through a sequencing platform, which may be chosen from, but is not limited to, the Hisq/Miseq/Nextseq sequencing platform (Illumina), the Ion Torrent platform (Thermo Fisher/Life Technologies), the BGISEQ platform (BGI) and single-molecule sequencing platforms. The sequencing method may be chosen from single-read sequencing and paired-end sequencing. The obtained sequencing results/data (i.e., read fragments) are referred to as reads. The length of a read is referred to as read length.

FIG. 1 shows a method for detecting a spot on an image according to an embodiment of the present disclosure. The image is acquired from a field of view having a plurality of nucleic acid molecules with optically detectable label in which a base extension reaction occurs, and at least a part of the nucleic acid molecules are presented as spots on the image. The method comprises: S10, preprocessing the image to give a preprocessed image; S20, determining a critical value to simplify the preprocessed image, so as to give a simplified image, comprising: assigning a first preset value to a pixel value of a pixel on the preprocessed image less than the critical value, and a second preset value to a pixel value of a pixel on the preprocessed image not less than the critical value; S30, determining a first spot detection threshold c1 based on the preprocessed image; and S40, identifying a candidate spot on the image based on the preprocessed image and the simplified image, comprising: determining a pixel matrix fulfilling at least two of the following conditions a)-c) as a candidate spot: a) in the preprocessed image, the center pixel of the pixel matrix has the maximum pixel value, the pixel matrix is represented by k1×k2, both k1 and k2 are odd numbers greater than 1, and the pixel matrix k1×k2 comprises k1×k2 pixels; b) in the simplified image, the pixel value of the center pixel of the pixel matrix is the second preset value, and the pixel connectivity in the pixel matrix is greater than ⅔×k1×k2; and c) in the preprocessed image, the pixel value of the center pixel of the pixel matrix is greater than a third preset value, g1*g2 is >c1, g1 is a correlation coefficient of two-dimensional Gaussian distribution in an area of m1×m2 centered on the center pixel of the pixel matrix, g2 is a pixel matrix in the area of m1×m2, both m1 and m2 are odd numbers greater than 1, and the area of m1×m2 comprises m1×m2 pixels.

The method for detecting a spot on an image, including the determining condition or a combination of determining conditions, is determined by the inventor through a large quantity of data training. According to the method, spots on the image can be detected quickly and effectively, especially for an image acquired from a field of view in which a nucleic acid sequencing reaction occurs. There is no special limitation on the to-be-detected image, or original input data. The method is applicable to processing and analysis of any images generated by a nucleic acid sequencing platform based on optical detection, including but not limited to second- and third-generation sequencing, and features high accuracy and high efficiency and more information about the sequence acquired from the image. Specifically, for a random image and signal identification requiring high accuracy, the method has special advantages.

For a grayscale image, pixel value refers to the grayscale value. A color image having three pixel values for each pixel may be converted into a grayscale image before detecting the spots, so as to reduce the calculation and complexity in an image detection process. A non-grayscale image may be converted into a grayscale image with methods including but not limited to floating point algorithm, integer method, shift method, mean value method.

In some specific embodiments, S10, preprocessing the image comprises: determining a background of the image using opening operation; converting the image into a first image based on the background using top-hat operation; performing Gaussian blur on the first image to give a second image; and sharpening the second image to give the preprocessed image. In this way, noise reduction of the image can be effectively performed or the signal-to-noise ratio of the image can be improved, which helps to accurately detect a spot.

Opening operation is a morphological process, and specifically, a process of sequential corrosion and expansion. The corrosion procedure reduces the foreground (a portion of interest), and the expansion procedure enlarges the foreground. The opening operation can be used to eliminate small objects, separate objects at a fine point, and smooth the boundary of a large object without significantly changing its area. In this embodiment, the size of a structural element p1×p2 (a basic template used to process the image) for opening operation on the image is not specifically defined, and p1 and p2 are odd numbers. In one example, the structural element p1×p2 may be 15×15, 31×31, or the like, and finally a preprocessed image that is beneficial for subsequent processing and analysis can be obtained.

The top-hat operation is usually used to separate plaques that are brighter than neighboring points (peaks/spots). When an image has a large area of background and regular small items, the background may be extracted using top-hat operation. In one example, the top-hat transformation of an image comprises: performing the opening operation on the image, and subtracting the opening operation result from the original image to give a first image, i.e., the image given by the top-hat transformation. The mathematical expression of top-hat transformation is dst=tophat(src,element)=src—open(src,element). The inventor believes that, the opening operation may enlarge cracks or blocks of low brightness. Therefore, subtracting opening operation result from the original image may highlight blocks brighter than surrounding blocks in the original image. The operation is related to the size of a selected kernel, in other words, related to the expected size of the peak/spot. If the peak has an unexpected size, the processing may lead to many small bumps on the whole image, and when referring to an image with virtual focus, messed peaks/spots. In one example, the expected size of the peak, or the size of the kernel, is 3×3, and the image acquired from top-hat transformation is conducive to subsequent denoising process.

Gaussian blur, also referred to as Gaussian filter, is a linear smoothing filter applicable for eliminating Gaussian noise, and is widely used in denoising of image processing. Generally speaking, the Gaussian filter is a process of weighted averaging on the whole image. A value of each pixel is a weighted average of the value itself and other pixel values in neighborhood. The specific procedure of the Gaussian filter is: scanning each pixel in the image using a template (also referred to as convolution or mask), and replacing the value of the center pixel of the template with a weighted average grayscale value of pixels in neighborhood determined using the template. In one example, the Gaussian blur is performed on the first image using GaussianBlur function in OpenCV. The Gaussian distribution parameter Sigma is 0.9, and the two-dimensional filter matrix (convolution kernel) used is 3×3. From a perspective of an image, after the Gaussian blur, the small bumps on the first image are smoothed, and edges of the image are smooth. Further, the second image, or the image acquired from Gaussian filter, is sharpened, for example, by two-dimensional Laplacian sharpening. From a perspective of an image, edges are sharpened after processing, and the image acquired from Gaussian blur is restored.

In some specific embodiments, S20 comprises: determining the critical value based on a background and the preprocessed image, and comparing a pixel value of a pixel on the preprocessed image with the critical value, and assigning a first preset value to a pixel value of a pixel on the preprocessed image less than the critical value and a second preset value to a pixel value of a pixel on the preprocessed image not less than the critical value, so as to give a simplified image. As such, according to the critical value determining manner and the critical value determined by summarizing a large amount of data, the preprocessed image is simplified, for example, by binarization, which may facilitate subsequent accurate spot detection, accurate base identification, high-quality data acquisition, and the like.

Specifically, in some specific embodiments, S20 comprises: dividing the result acquired from sharpening by the result of opening operation in S10, to give a set of values corresponding to pixels of the image; and determining, based on the set of values, a critical value of the image acquired from binarization. For example, the set of values may be sorted in ascending order, and the 20th, 30th or 40th percentile in the set of values may serve as the binarization critical value/threshold. As such, the binary image may facilitate subsequent accurate detection and identification of spots.

In one example, the structural element for opening operation of image preprocessing in S10 is p1×p2, and the preprocessed image (the result of sharpening) is divided by the result of opening operation, to give a set of arrays/matrices p1×p2 of the same size as the structural element. The p1×p2 values comprised in each array are sorted in ascending order, and the 30th percentile in the array serves as the binarization critical value/threshold of the block (numerical matrix). As such, a threshold is determined for binarization in each block of the image, and the final binarization result highlights real information while denoising, which helps to accurately detect spots.

In some specific embodiments, S30 comprises: determining a first spot detection threshold by Otsu's method. The Otsu's method, or Otsu's algorithm, maximizes the inter-class variance to segment an image, which indicates fewer segmentation errors and high accuracy. It is assumed that the segmentation threshold of the foreground and the background of the preprocessed image is T(c1), the proportion of pixels in the foreground to the whole image is $w_0$ with the average grayscale value being $\rho_0$, and the proportion of pixels in the background to the whole image is $w_1$ with the average grayscale value being $\rho_1$. The overall average grayscale value of the to-be-processed image is denoted as, and the inter-class variance is denoted as var, which are: $\mu=\omega_0*\mu_0+\omega_1*\mu_1$ $var=\omega_0(\mu_0-\mu)^2+\omega_1(\mu_1-\mu)^2$. The latter is substituted into the former, giving the following equation: $var=\omega_0\omega_1(\mu_1-\mu_0)^2$. The segmentation threshold T that enables the interclass variance to be maximum is given by a traversal method, and is the required first spot detection threshold c1.

In some specific embodiments, S40, identifying a candidate spot on the image based on the preprocessed image and the simplified image, comprises determining a pixel matrix fulfilling at least two of the conditions a) to c) as the candidate spot. As such, the accuracy of subsequent nucleic acid sequencing based on spot information and the quality of reads may be effectively improved.

Specifically, in one example, conditions required for determining a candidate spot include a), wherein k1 and k2 may or may not be equal. In one example, related parameters of an imaging system includes: a 60× magnification for objective lens, an electronic sensor size of 6.5 μm, the smallest identifiable size of 0.1 μm for a microscopic image acquired by an electronic sensor, output or input 16-bit grayscale or color images of 512×512, 1024×1024 or 2048×2048, and a range of greater than 1 to less than 10 for k1 and k2. In one example, in a preprocessed image, k1 and k2 are set at 3 according to the expected size of spot; and in another example, k1 and k2 are set at 5.

In one example, conditions required for determining a candidate spot include b). In the simplified image, the pixel value of the center pixel of the pixel matrix is the second preset value, and the pixel connectivity of the pixel matrix is greater than ⅔×k1×k2, in other words, the pixel value of the center pixel is greater than the critical value, and the pixel connectivity is greater than two thirds of the matrix. Herein, two or more adjacent pixels having a pixel value of the second preset value are referred to as connected pixels/pixel connectivity. For example, the simplified image is a binary image, the first preset value is 0, and the second preset value is 1. As shown in FIG. 2, a bold and enlarged point represents the center of the pixel matrix, and a thick frame represents a pixel matrix 3×3, i.e., k1=k2=3. The pixel value of the center pixel of the matrix is 1, and the pixel connectivity is 4 (less than ⅔×k1×k2=6). The pixel matrix does not fulfill the condition b), and the spot is not the candidate spot.

In one example, conditions required for determining a candidate spot include c). In the preprocessed image, g2 is a corrected pixel matrix in the area of m1×m2, i.e., a sum of corrected pixels in the area of m1×m2. In one example, the correction is performed based on the proportion of pixels of the second preset pixel value in the corresponding area of m1×m2 in the simplified image. For example, as shown in FIG. 3, m1=m2=5, the proportion of pixels of the second preset pixel value in the corresponding area of m1×m2 in the simplified image is 13/25 (there are 13 "1"s), and thus the corrected g2 is 13/25 of the original. As such, it facilitates accuracy of the spot detection and identification, and subsequent analysis and interpretation of spot information.

In some specific embodiments, as shown in FIG. 4, the method further comprises S50, determining whether the candidate spot is a spot. In one example, S50 comprises: determining a second spot detection threshold based on the preprocessed image, and determining a candidate spot of a pixel value not less than the second spot detection threshold as a spot. In one specific example, a pixel value of a pixel to which the coordinates of the candidate spot correspond is assigned to the pixel value of the candidate spot. After the candidate spots are further screened using the second spot detection threshold determined based on the preprocessed image, at least a part of spots that are more likely the image background but are similar to "spots" in brightness (intensity) and/or shape may be excluded, which helps to accurately identify a sequence based on the spot, and improves quality of reads.

In one example, the coordinates of the candidate spot may be given by centroid method, including sub-pixel coordinates. The grayscale value of a coordinates location of the candidate spot is calculated by bilinear interpolation.

In some specific examples, S50 comprises: dividing the preprocessed image into a set of block of a predetermined size; sorting pixels in the block by pixel value to determine a second spot detection threshold corresponding to the block; and determining a candidate spot in the block of a pixel value not less than the second spot detection threshold corresponding to the block as the spot. As such, a difference between different blocks of the image such as an overall difference of light intensity is distinguished, and each spot is further detected and identified, so as to help to accurately identify the spot and find more spots.

When dividing the preprocessed image into a set of block of a predetermined size, the blocks may or may not overlap with each other. In one example, the blocks do not overlap with each other. In some embodiments, the size of the preprocessed image is not less than 512×512, such as 512×512, 1024×1024, 1800×1800, or 2056×2056, and the block of the predetermined size may be set as 200×200. As such, the spot is quickly calculated, determined, and identified.

Figure 5:
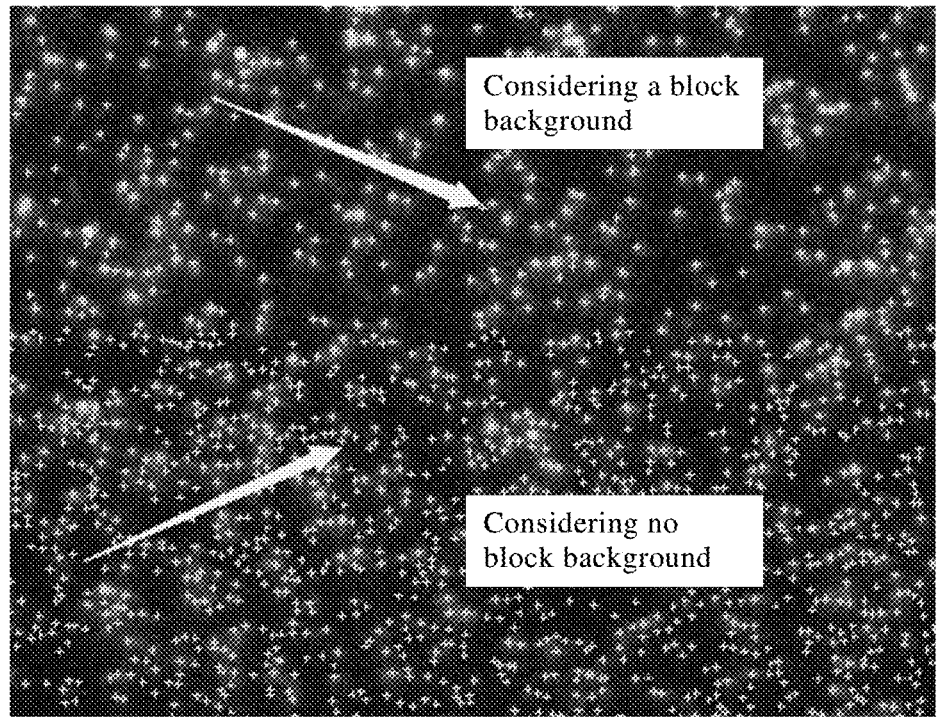
FIG. 5 is a schematic diagram of spot detection results with or without S50 according to a specific embodiment of the present disclosure.

In some embodiments, when determining a second spot detection threshold corresponding to the block, pixel values of pixels in each block are sorted in ascending order. The p10+(p10−p1)×4.1 is used as the second spot detection threshold corresponding to the block, i.e., a background of the block, p1 represents the first percentile, and p10 represents the tenth percentile. The threshold is a relatively stable threshold given by the inventor through a large amount of data training test, which can eliminate a majority of spots on the background. It can be understood that when an optical system is adjusted and overall pixel distribution of the image changes, the threshold may need appropriate adjustment. FIG. 5 is a schematic comparison of before and after S50, i.e., schematic diagrams of spot detection results given before and after spots on a block background are eliminated. The upper panel of FIG. 5 is a spot detection result after S50 is performed, and the lower panel is a spot detection result when S50 is not performed. The cross mark indicates a candidate spot or spot.

Logic and/or steps shown in the flowcharts or described herein in other manners, for example, may be considered as a program list of executable instructions that are used to implement logical functions, and may be specifically implemented on any computer-readable storage medium, for an instruction execution system, device, or device (for example, a computer-based system, a system including a processor, or another system that can fetch instructions from the instruction execution system, device, or device and execute the instructions), or for a combination of the instruction execution system, device, or device. As used herein, the "computer-readable storage medium" may be any device that may include, store, communicate, propagate, or transmit a program for a instruction execution system, device, or device, or for a combination of the instruction execution system, device, or device. More specific examples (this list is not exhaustive) of the computer-readable storage medium include the following: an electrical connection (an electrical device) with one or more buses, a portable computer cartridge (an magnetic device), a random-access memory (RAM), a read-only memory (ROM), an electrically erasable programmable read-only memory (EPROM or flash memory), an optical fiber device, and a compact disc read-only memory (CDROM). In addition, the computer-readable storage medium may even be a piece of paper on which the programs can be printed or any other appropriate media, because, for example, the paper or the media may be optically scanned, and the program may be electrically acquired by processing such as edition, decoding, or any other appropriate means when necessary and then stored in a computer storage.

Figure 6:
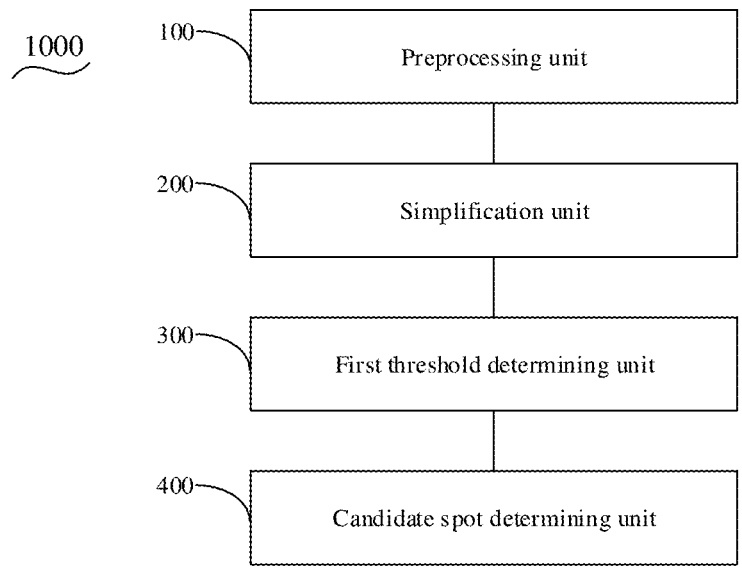
FIG. 6 is a schematic diagram of an device for detecting a spot on an image according to a specific embodiment of the present disclosure.

FIG. 6 shows an device 1000 for detecting a spot on an image in an embodiment of the present disclosure. The device is configured for implementing the method for detecting a spot on an image according to any of the above embodiments. The image is acquired from a field of view having a plurality of nucleic acid molecules with optically detectable label in which a base extension reaction occurs, and at least a part of the nucleic acid molecules are presented as spots on the image. The device comprises: a preprocessing unit 100 configured for preprocessing the image to give a preprocessed image; a simplification unit 200 configured for: determining a critical value to simplify the image preprocessed by the preprocessing unit, so as to give a simplified image, comprising: assigning a first preset value to a pixel value of a pixel on the preprocessed image less than the critical value, and a second preset value to a pixel value of a pixel on the preprocessed image not less than the critical value; a first threshold determining unit 300, configured for determining a first spot detection threshold c1 based on the image preprocessed by the preprocessing unit; and a candidate spot determining unit 400, configured for identifying a candidate spot on the image based on the image preprocessed by the preprocessing unit and the image simplified by the simplification unit, comprising: determining a pixel matrix fulfilling the following conditions as a candidate spot: a) in the preprocessed image, the center pixel of the pixel matrix has the maximum pixel value, the pixel matrix is represented by k1×k2, both k1 and k2 are odd numbers greater than 1, and the pixel matrix k1×k2 comprises k1×k2 pixels; b) in the simplified image, the pixel value of the center pixel of the pixel matrix is the second preset value, and the pixel connectivity in the pixel matrix is greater than ⅔×k1×k2; and c) in the preprocessed image, the pixel value of the center pixel of the pixel matrix is greater than a third preset value, g1*g2 is >c1, g1 is a correlation coefficient of two-dimensional Gaussian distribution in an area of m1×m2 centered on the center pixel of the pixel matrix, g2 is a pixel matrix in the area of m1×m2, both m1 and m2 are odd numbers greater than 1, and the area of m1×m2 comprises m1×m2 pixels.

The above description of the advantages and technical features of the method for detecting a spot on an image in any embodiment of the present disclosure is also applicable to the spot detection device in this embodiment of the present disclosure, and will not be repeated hereinafter.

Figure 7:
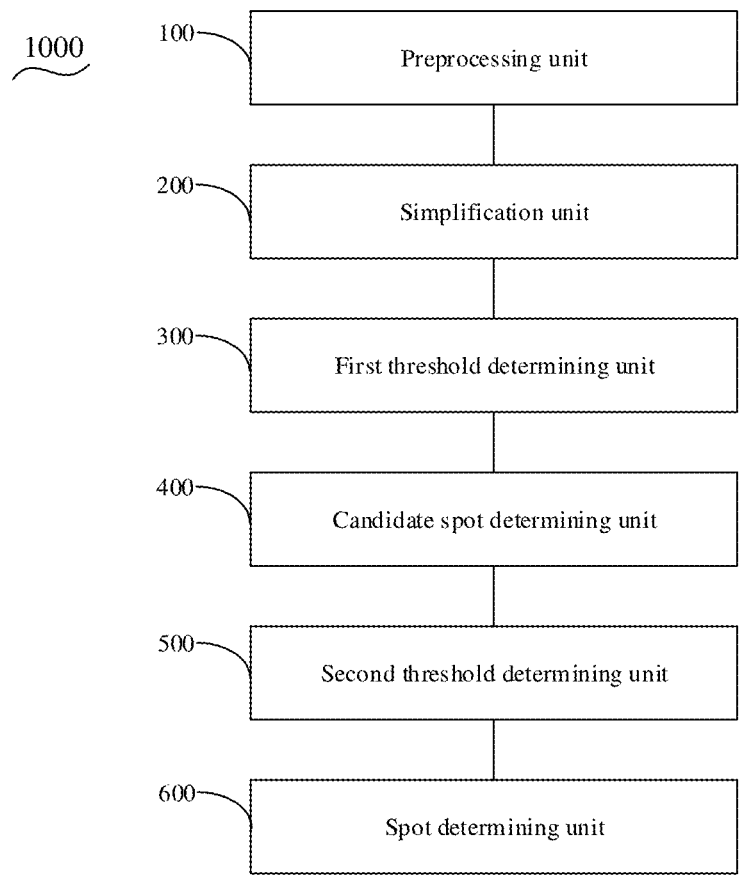
FIG. 7 is a schematic diagram of an device for detecting a spot on an image according to a specific embodiment of the present disclosure.

For example, as shown in FIG. 7, in some examples, the device 1000 further comprises a second threshold determining unit 500 and a spot determining unit 600. The second threshold determining unit 500 is configured for determining a second spot detection threshold based on the image preprocessed by the preprocessing unit; and the spot determining unit 600 is configured for determining a candidate spot of a pixel value not less than the second spot detection threshold as a spot.

In some examples, a pixel value of the candidate spot is a pixel value of a pixel to which coordinates of the candidate spot correspond.

In some examples, the second threshold determining unit 500 is configured for: dividing the preprocessed image into a set of block of a predetermined size, and sorting pixels in the block by pixel value to determine a second spot detection threshold corresponding to the block; and the spot determining unit is configured for: determining a candidate spot in the block of a pixel value not less than the second spot detection threshold corresponding to the block as the spot.

In some examples, the preprocessing unit 100 is configured for: determining a background of the image using opening operation; converting the image into a first image based on the background using top-hat operation; performing Gaussian blur on the first image to give a second image; and sharpening the second image to give the preprocessed image.

In some examples, the simplification unit 200 is configured for: determining the critical value based on the background and the preprocessed image; and comparing a pixel value of a pixel on the preprocessed image with the critical value, so as to give a simplified image.

In some examples, g2 is a corrected pixel matrix in the area of m1×m2, and pixels in the area of m1×m2 are corrected based on the proportion of pixels of the second preset pixel value in the corresponding area of m1×m2 in the simplified image.

One embodiment of the present disclosure further provides a computer program product comprising an instruction for detecting a spot on an image, wherein the instruction causes the computer to execute all or a part of the steps of the spot detection method in any of the above embodiments when the program is executed in the computer.

It will be appreciated by those skilled in the art know that, in addition to implementing the controller/processor in a form of computer-readable program code, same functions can be implemented in a form of a logic gate, a switch, an application-specific integrated circuit, an editable logic controller, an embedded microcontroller, and the like by logically programming the steps. Therefore, the controller/processor may be regarded as a hardware component, and an device included in the controller/processor for implementing various functions may also be regarded as a structure in the hardware component. Alternatively, an device for implementing various functions may be regarded as both a software module for implementing the method and a structure in the hardware component.

In the specification, descriptions such as "one embodiment", "some embodiments", "one or some specific embodiments", "one or some examples", "exemplary" or the like, means that a particular feature, structure or characteristic described in reference to the embodiment or example is included in at least one embodiment or example of the present disclosure. In this specification, the schematic description of the aforementioned terms do not necessarily refer to the same embodiment or example. Moreover, the specific features, structures and other characteristics described may be combined in any one or more embodiments or examples in an appropriate manner.

Although the embodiments of the present disclosure have been illustrated and described, it can be understood by those of ordinary skill in the art that various changes, modifications, replacements and variations can be made to these embodiments without departing from the principle and purpose of the present disclosure, and the scope of the present disclosure is defined by the claims and equivalents therefore.

The invention claimed is:

1. A method for detecting a spot on an image, wherein the image is acquired from a field of view having a plurality of nucleic acid molecules with optically detectable label in which a base extension reaction occurs, and at least a part of the nucleic acid molecules are presented as spots on the image, the method comprising:
preprocessing the image to give a preprocessed image;
determining a critical value to simplify the preprocessed image, so as to give a simplified image, comprising: assigning a first preset value to a pixel value of a pixel on the preprocessed image less than the critical value, and assigning a second preset value to a pixel value of a pixel on the preprocessed image not less than the critical value;
identifying a candidate spot on the image based on the preprocessed image and the simplified image, comprising: determining a pixel matrix fulfilling the following conditions a) and b) as the candidate spot:
a) in the preprocessed image, the center pixel of the pixel matrix has the maximum pixel value, the pixel matrix is represented by k1×k2, both k1 and k2 are odd numbers greater than 1, and the pixel matrix k1×k2 comprises k1×k2 pixels; and
b) in the simplified image, the pixel value of the center pixel of the pixel matrix is the second preset value, and the pixel connectivity in the pixel matrix is greater than $\frac{2}{3}\times k1 \times k2$.

2. The method according to claim 1, wherein preprocessing the image comprises:
determining a background of the image using opening operation;
converting the image into a first image based on the background using top-hat operation;
performing Gaussian blur on the first image to give a second image; and
sharpening the second image to give the preprocessed image.

3. The method according to claim 2, wherein determining a critical value to simplify the preprocessed image, so as to give a simplified image, comprises:
determining the critical value based on the background and the preprocessed image; and
comparing a pixel value of a pixel on the preprocessed image with the critical value, so as to give a simplified image.

4. A device for detecting a spot on an image, wherein the image is acquired from a field of view having a plurality of nucleic acid molecules with optically detectable label in which a base extension reaction occurs, and at least a part of the nucleic acid molecules are presented as spots on the image, the device comprising:
a preprocessing unit configured for preprocessing the image to give a preprocessed image;
a simplification unit configured for: determining a critical value to simplify the image preprocessed by the preprocessing unit, so as to give a simplified image, comprising: assigning a first preset value to a pixel value of a pixel on the preprocessed image less than the critical value, and a second preset value to a pixel value of a pixel on the preprocessed image not less than the critical value; and
a candidate spot determining unit configured for identifying a candidate spot on the image based on the image preprocessed by the preprocessing unit and the image simplified by the simplification unit, comprising: determining a pixel matrix fulfilling the following conditions as the candidate spot:
a) in the preprocessed image, the center pixel of the pixel matrix has the maximum pixel value, the pixel matrix is represented by k1×k2, both k1 and k2 are odd numbers greater than 1, and the pixel matrix k1×k2 comprises k1×k2 pixels; and
b) in the simplified image, the pixel value of the center pixel of the pixel matrix is the second preset value, and the pixel connectivity in the pixel matrix is greater than $\frac{2}{3}\times k1 \times k2$.

5. The device according to a claim 4, wherein the preprocessing unit is configured for:
determining a background of the image using opening operation;
converting the image into a first image based on the background using top-hat operation;
performing Gaussian blur on the first image to give a second image; and sharpening the second image to give the preprocessed image.

6. The device according to claim 5, wherein the simplification unit is configured for:
determining the critical value based on the background and the preprocessed image; and comparing a pixel value of a pixel on the preprocessed image with the critical value, so as to give a simplified image.

7. A non-transitory computer program product, comprising a program stored thereon having instructions for detecting a spot on an image, wherein the instructions cause a computer to execute the method according to claim 1 when the program is executed in the computer.

8. The method according to claim 1, further comprising: determining a first spot detection threshold $c1$ based on the preprocessed image; and identifying a candidate spot on the image based on the preprocessed image and the simplified image, further comprising: determining the pixel matrix fulfilling the following condition c) as the candidate spot:

c) in the preprocessed image, the pixel value of the center pixel of the pixel matrix is greater than a third preset value, $g1*g2$ is $>c1$, $g1$ is a correlation coefficient of two-dimensional Gaussian distribution in an area of $m1 \times m2$ centered on the center pixel of the pixel matrix, $g2$ is a pixel matrix in the area of $m1 \times m2$, both $m1$ and $m2$ are odd numbers greater than 1, and the area of $m1 \times m2$ comprises $m1 \times m2$ pixels.

9. The method according to claim 8, further comprising: determining whether the candidate spot is the spot, comprising:

determining a second spot detection threshold based on the preprocessed image, and determining a candidate spot of a pixel value not less than the second spot detection threshold as the spot.

10. The method according to claim 9, wherein the pixel value of the candidate spot is a pixel value of a pixel to which coordinates of the candidate spot correspond.

11. The method according to claim 9, wherein determining a second spot detection threshold based on the preprocessed image, and determining a candidate spot of a pixel value not less than the second spot detection threshold as the spot comprises:

dividing the preprocessed image into a set of block of a predetermined size;
sorting pixels in the block by pixel value to determine the second spot detection threshold corresponding to the block; and
determining a candidate spot in the block of a pixel value not less than the second spot detection threshold corresponding to the block as the spot.

12. The method according to claim 8, wherein $g2$ is a corrected pixel matrix in the area of $m1 \times m2$, and the correction is performed based on the proportion of pixels of the second preset pixel value in the corresponding area of $m1 \times m2$ in the simplified image.

13. The device according to claim 4, further comprising:
a first threshold determining unit configured for determining a first spot detection threshold $c1$ based on the image preprocessed by the preprocessing unit; and
a candidate spot determining unit configured for identifying a candidate spot on the image based on the image preprocessed by the preprocessing unit and the image simplified by the simplification unit, further comprising: determining the pixel matrix fulfilling the following condition c) as the candidate spot:
c) in the preprocessed image, the pixel value of the center pixel of the pixel matrix is greater than a third preset value, $g1*g2$ is $>c1$, $g1$ is a correlation coefficient of two-dimensional Gaussian distribution in an area of $m1 \times m2$ centered on the center pixel of the pixel matrix, $g2$ is a pixel matrix in the area of $m1 \times m2$, both $m1$ and $m2$ are odd numbers greater than 1, and the area of $m1 \times m2$ comprises $m1 \times m2$ pixels.

14. The device according to claim 13, further comprising a second threshold determining unit and a spot determining unit, wherein the second threshold determining unit is configured for determining a second spot detection threshold based on the image preprocessed by the preprocessing unit; and
the spot determining unit is configured for determining a candidate spot of a pixel value not less than the second spot detection threshold as the spot.

15. The device according to claim 14, wherein the pixel value of the candidate spot is a pixel value of a pixel to which coordinates of the candidate spot correspond.

16. The device according to claim 14, wherein the second threshold determining unit is configured for: dividing the preprocessed image into a set of block of a predetermined size, and sorting pixels in the block by pixel value to determine the second spot detection threshold corresponding to the block; and the spot determining unit is configured for determining a candidate spot in the block of a pixel value not less than the second spot detection threshold corresponding to the block as the spot.

17. The device according to claim 13, wherein $g2$ is a corrected pixel matrix in the area of $m1 \times m2$, and pixels in the area of $m1 \times m2$ are corrected based on the proportion of pixels of the second preset pixel value in the corresponding area of $m1 \times m2$ in the simplified image.

* * * * *